(12) United States Patent
Saitou et al.

(10) Patent No.: US 6,451,005 B1
(45) Date of Patent: Sep. 17, 2002

(54) CATHETER

(75) Inventors: Takehiko Saitou; Nobuaki Mihara, both of Fujinomiya (JP)

(73) Assignee: Terumo Kabushiki Kaisha, Tokyo (JP)

( * ) Notice: Subject to any disclaimer, the term of this patent is extended or adjusted under 35 U.S.C. 154(b) by 1 day.

(21) Appl. No.: 09/777,709

(22) Filed: Feb. 7, 2001

(30) Foreign Application Priority Data

Feb. 9, 2000 (JP) ........................................ 2000-038023

(51) Int. Cl.[7] .............................................. A61M 25/00
(52) U.S. Cl. ...................................................... 604/526
(58) Field of Search .................................. 604/524, 526

(56) References Cited

U.S. PATENT DOCUMENTS

| | | |
|---|---|---|
| 4,981,478 A | 1/1991 | Evard et al. |
| 5,538,513 A | 7/1996 | Okajima |
| 5,662,622 A | 9/1997 | Gore et al. |
| 5,695,483 A * | 12/1997 | Samson ................ 604/526 |
| 5,711,909 A | 1/1998 | Gore et al. |
| 5,782,809 A | 7/1998 | Umeno et al. |
| 5,827,242 A | 10/1998 | Follmer et al. |
| 5,851,203 A | 12/1998 | Van Muiden |
| 6,258,080 B1 * | 7/2001 | Samson ................ 604/526 |

FOREIGN PATENT DOCUMENTS

| | | |
|---|---|---|
| EP | 0 622 385 | 7/1995 |
| JP | 9-94296 | 4/1997 |
| WO | 97/17998 | 6/1997 |

* cited by examiner

*Primary Examiner*—Philippe Derakshani
(74) *Attorney, Agent, or Firm*—Burns, Doane, Swecker & Mathis, LLP (57) ABSTRACT

A catheter has a flexible tubular body and a reinforcing coil embedded in a wall of said body, wherein said catheter has an outer diameter not larger than 1.5 mm at a front end thereof, said body has a first region disposed within a range of 1–30 mm from said front end of said catheter and a second region nearer to a rear end of said catheter than said first region; said coil extends from a position inside said first region to said second region; a part of said coil disposed in said second region is wound at long winding pitches; and a winding pitch of a part of said coil disposed in said first region is shorter than that of the part of the coil disposed in said second region and becomes shorter gradually or step-wise toward said front end of said catheter, whereby a rigidity of said catheter is lower in said first region than in said second region.

39 Claims, 5 Drawing Sheets

CATHETER

BACKGROUND OF THE INVENTION

The present invention relates to a catheter which is used by inserting it into a blood vessel or the like.

In recent years, the use of the catheter is popular to treat lesion of a blood vessel because the catheter has a very low degree of a surgical stress.

In using the catheter, the catheter is required to have a high operability because it is necessary to insert it into a blood vessel having a fine and complicated pattern at a high speed and with a reliable selectivity.

It is also demanded that the catheter has a small diameter, i,e., has a possible smallest outer diameter, with a certain inner diameter secured to widen the selection range of an insertion portion in the human body, reduce the burden of a patient, and improve an insertion operability.

A micro-catheter is used to administer or inject medicines, thrombus substances to be used in an operation which is called embolization to be performed in a blood vessel or a contrast medium to a desired portion in internal organs (liver) such as brain and belly to diagnose and treat the desired portion. It is necessary to advance the micro-catheter inside a peripheral blood vessel narrow, branching, and zigzag and having a diameter less than 3 mm and introduce it into the desired portion selectively. In recent years, owing to medical progress, it is necessary to inject medicines, thrombus substances or a contrast medium to diagnose and treat the desired portion by inserting the micro-catheter to a peripheral blood vessel having a diameter as small as less than 1 mm. Therefore, there is a demand for development of the catheter which can be inserted into such a narrow blood vessel.

The operability of the catheter will be described below. The catheter is required to have pressing performance of reliably transmitting a pressing force applied by an operator to advance the catheter inside a blood vessel to the front end thereof from the rear end thereof; torque transmission performance of transmitting a rotational force applied to the rear end of the catheter to its front end; follow-up performance of progressing smoothly and reliably inside the curved blood vessel along a guide wire; and kink resistance of being not bent at a portion where the blood vessel is curved or bent after the guide wire is pulled out from the catheter at the desired portion. The catheter is also required to have safety that the tip of the catheter does not damage the inner wall of the blood vessel.

The catheter is also required to have pressure resistance to prevent it from bursting even when a contrast medium or the like is injected thereinto at a high pressure.

It is known that to obtain the pressing performance and the torque transmission performance, the part of the catheter except the front end thereof is composed of a comparatively hard material. It is also known that to obtain the follow-up performance and the safety, the front end of the catheter is composed of a comparatively soft material.

In particular, it is demanded that to obtain high follow-up performance, a region having a length of about 5 mm rearward from the front end of the catheter is flexible (low in rigidity) and bendable.

However, in the case where the front end of the catheter is composed of the comparatively flexible material, it is difficult to allow the front end of the catheter to have high kink resistance and pressure resistance. That is, it is difficult for the conventional art to allow the catheter to have all of these characteristics at the same time. The case where a contrast medium or the like is injected into a blood vessel or the like at a high pressure is described below. Normally, a high pressure is applied to the rear end of the catheter. Thus it is important that the catheter has an appropriate pressure resistance at its rear end. If a lumen at the front end of the catheter is clogged with the contrast medium for some reason, a high pressure is applied to the front end of the catheter. As a result, there is a possibility that the catheter bursts at the front end thereof. Accordingly, the catheter is demanded to have a pressure resistance, at its front end, equal to that at its rear end.

To confirm the position of the front end of the catheter under X-ray fluoroscopy, there is commercially available a catheter having a radiopaque marker consisting of a radiopaque cylindrical band made of platinum or the like or a radiopaque coil, made of platinum or the like, wound with adjacent windings in contact with each other. The radiopaque marker is installed at a position spaced about 1 mm apart from the front end of the catheter. However, because the radiopaque marker is made of a material having a high rigidity, the radiopaque marker reduces the flexibility and follow-performance at the front end of the catheter. The front end of a micro-catheter is very small in its diameter and very flexible to allow it to advance it inside a very narrow blood vessel branching and zigzag complicatedly. Thus, the radiopaque marker having a length of only 1 mm considerably reduces the flexibility of the catheter at a region about 5 mm apart from the front end thereof, thus sacrificing the operability of the catheter.

It is an object of the present invention to provide a catheter having high pressing performance, follow-up performance, and kink resistance. It is another object of the present invention to provide a catheter bendable and high in follow-up performance, with a front end thereof having high kink resistance and pressure resistance. It is still another object of the present invention to provide a catheter having a construction allowing its diameter to be small so that it is suitably used as a micro-catheter.

SUMMARY OF THE INVENTION

The object of this invention is to provide a catheter that has a flexible tubular body and a reinforcing coil embedded in a wall of said body, wherein said catheter has an outer diameter not larger than 1.5 mm at a front end thereof, said body has a first region disposed within a range of 1–30 mm from said front end of said catheter and a second region nearer to a rear end of said catheter than said first region; said coil extends from a position inside said first region to said second region; a part of said coil disposed in said second region is wound at long winding pitches; and a winding pitch of a part of said coil disposed in said first region is shorter than that of the part of the coil disposed in said second region and becomes shorter gradually or stepwise toward said front end of said catheter, whereby a rigidity of said catheter is lower in said first region than in said second region.

Further, the object of this invention is to provide a catheter that has a flexible tubular body and a reinforcing coil embedded in a wall of said body, wherein said catheter has an outer diameter not larger than 1.5 mm at a front end thereof, a front end of said coil is located within 1–30 mm apart from a front end of said body; a winding pitch of a part of said coil disposed within 1–30 mm apart from said front end of said body becomes shorter gradually or stepwise toward said front end of said catheter.

DETAILED DESCRIPTION OF THE PREFERRED EMBODIMENTS

A preferred embodiment of the catheter of the present invention will be described in detail below with reference to the accompanied drawings.

The embodiment will be described below by setting the right end in FIGS. 1 through 3 to the "rear end" and the left end therein to the "front end".

A catheter 1 of the embodiment has a tubular flexible body 2; and a coil 3 disposed in the body 2 and having a reinforcing effect. The catheter 1 has a first region 4 disposed at its front end and a second region 5 disposed nearer to its rear end than the first region 4. The coil 3 extends from the first region 4 to the second region 5. In the second region 5, the entire coil 3 is wound at relatively long winding pitches. In the first region 4, the winding pitch of the coil 3 is relatively short with the winding pitch becoming gradually or stepwise shorter toward the front end of the catheter 1. Thereby the rigidity (flexural rigidity) of the catheter 1 is lower in the first region 4 than in the second region 5.

The catheter 1 of the present invention has the flexible tubular body 2 and the reinforcing coil 3 embedded in a wall of the body 2. The catheter 1 has an outer diameter not larger than 1.5 mm at its front end. The body 2 has the first region 4 disposed within the range of 1–30 mm from the front end of the catheter 1 and the second region 5 nearer to the rear end of the catheter 1 than the first region 4. The coil 3 extends from a position inside the first region 4 to the second region 5. A part of the coil 3 disposed in the second region 5 is wound at long winding pitches. The winding pitch of a part of the coil 3 disposed in the first region 4 is shorter than that of the part of the coil 3 disposed in the second region 5. The winding pitch of the part of the coil 3 disposed in the first region 4 becomes shorter gradually or stepwise toward the front end of the catheter 1. Thereby the rigidity of the catheter 1 is lower in the first region 4 than in the second region 5.

The catheter 1 of the present invention has the tubular flexible body 2 and the reinforcing coil 3 embedded in the wall of the body 2. The catheter 1 has an outer diameter not larger than 1.5 mm at its front end. The front end of the coil 3 is located within 1–30 mm apart from the front end of the body 2. The winding pitch of the part of the coil 3 disposed within 1–30 mm apart from the front end of the body 2 becomes shorter gradually or stepwise toward the front end of the catheter 1.

Figure 2:
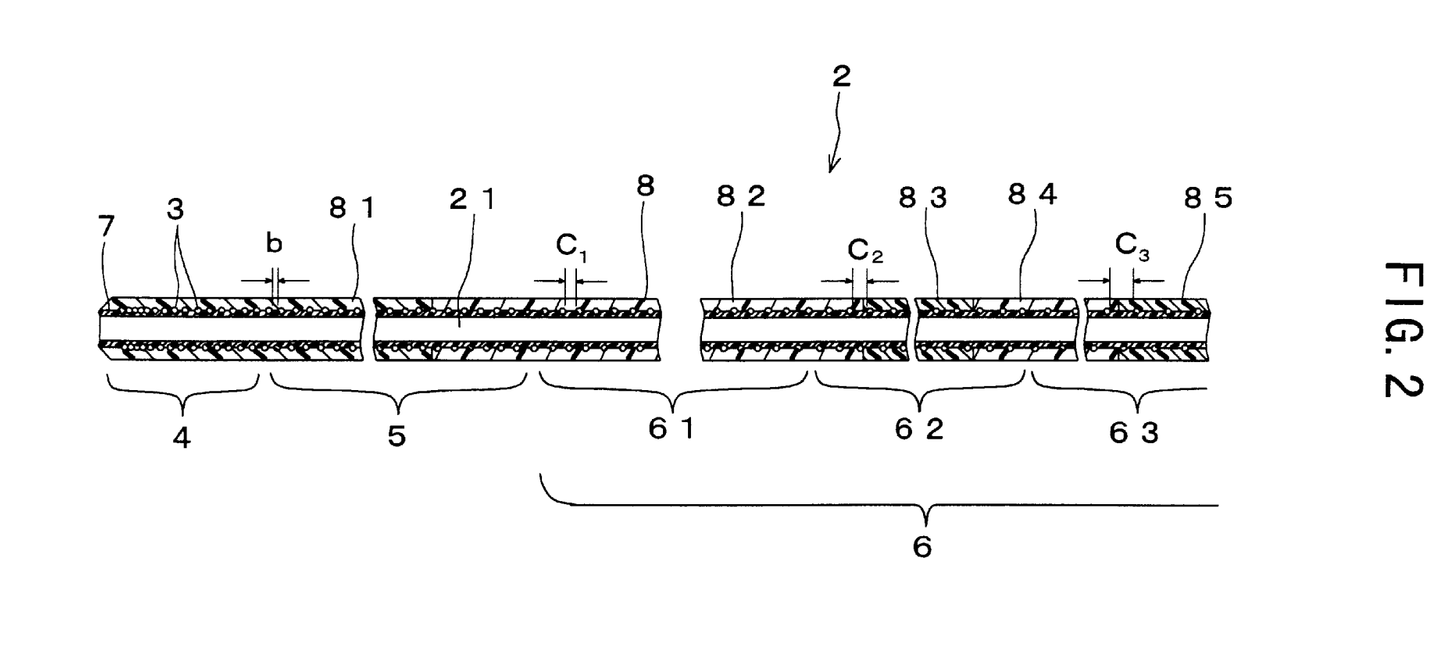
FIG. 2 is a sectional view, showing the catheter shown in FIG. 1, in which a part of the catheter is unshown.
Figure 3:
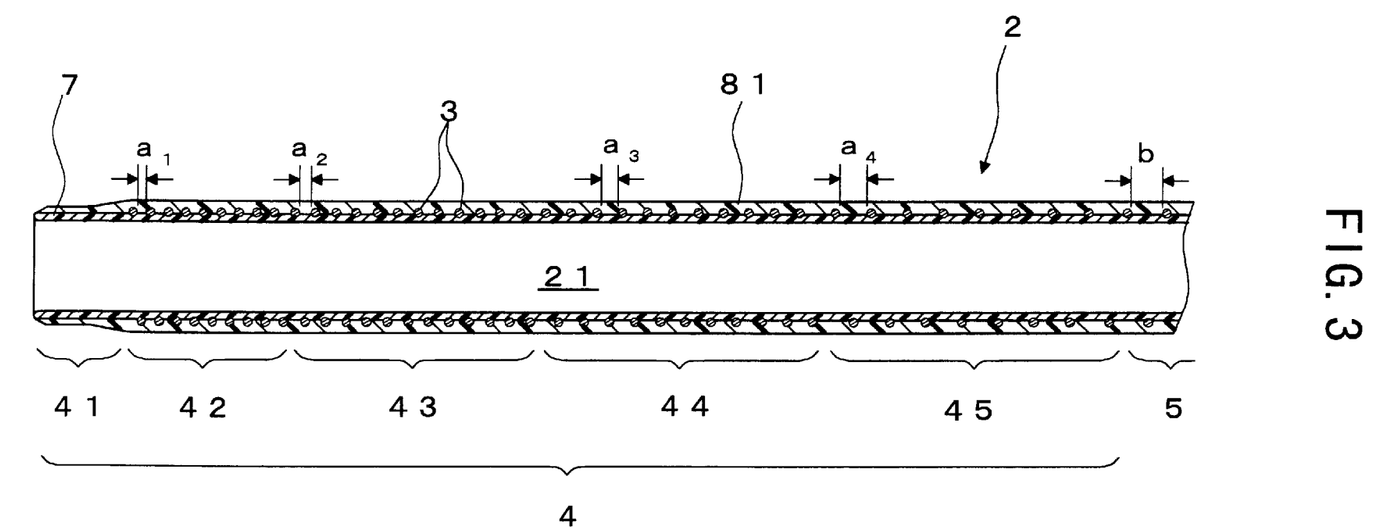
FIG. 3 is an enlarged sectional view showing a front side of the catheter shown in FIG. 1.

As shown in FIGS. 2 and 3, the winding pitch of the coil 3 described in the specification means the distance between adjacent windings of the coil 3 in the longitudinal direction of the catheter 1. That is, the winding pitch of the coil 3 means the length (interval) of the gap between adjacent windings of the coil 3 in the longitudinal direction of the catheter 1.

The catheter 1 of the embodiment will be described below in detail with reference to the accompanied drawings.

Figure 1:
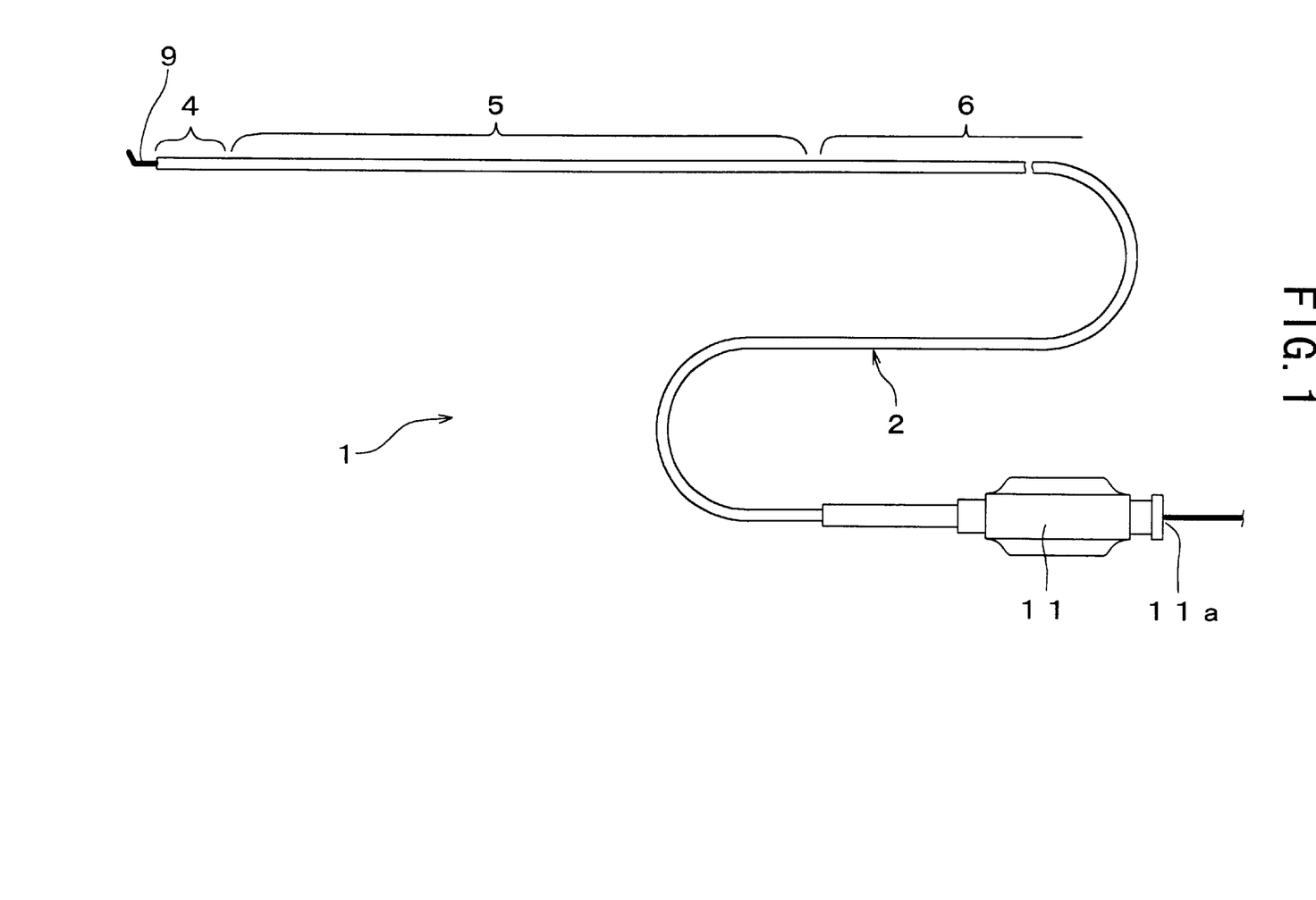
FIG. 1 is a plan view showing an entire catheter according to an embodiment of the present invention.

The catheter shown in FIG. 1 includes the body 2 and a hub 11 mounted on the rear end of the body 2.

The body 2 is composed of a flexible tubular member. A lumen 21 is formed inside the body 2 from its rear end to its front end. The lumen 21 functions as an inner lumen for inserting a guide wire thereinto. As shown in FIG. 1, a guide wire 9 is inserted into the lumen 21 when the catheter 1 is inserted into a blood vessel. The lumen 21 may be used as a passage for a medicine, thrombus substance, a contrast medium.

The hub 11 functions as an insertion opening for inserting the guide wire 9 into the lumen 21, an injection opening for injecting the medicine, thrombus substance, the contrast medium into the lumen 21, and a gripping portion of the catheter 1 in operating it.

The catheter 1 has the first region 4 and the second region 5 disposed nearer to the rear end of the catheter 1 than the first region 4. The first region 4 extends from the front end of the body 2 to its rear end. The second region 5 is adjacent to the first region 4 and extends from the front end of the body 2 to its rear end. The catheter 1 has a third region disposed nearer to the rear end of the body 2 than the second region 5. The third region 6 is adjacent to the second region 5 and extends to the rear end of the body 2.

As shown in FIG. 3, the first region 4 of the catheter 1 of the embodiment has a region 41 positioned at the front end of the body 2, a region 42 positioned nearer to the rear end of the body 2 than the region 41 and adjacent to the region 41, a region 43 positioned nearer to the rear end of the body 2 than the region 42 and adjacent to the region 42, a region 44 positioned nearer to the rear end of the body 2 than the region 43 and adjacent to the region 43, and a region 45 positioned nearer to the rear end of the body 2 than the region 44 and adjacent to the region 44.

As shown in FIGS. 2 and 3, the coil 3 having the reinforcing effect is embedded in the body 2. The coil 3 extends from the first region 4 to the second region 5 and to the third region 6 and reaches the rear end of the body 2.

The coil 3 is composed of a metal member and/or a non-metal member. For example, the coil 3 can be composed of a spiral metal member, a spiral non-metal member or a combination of the spiral metal member and the spiral non-metal member laminated thereon.

As materials for composing the metal member, it is possible to singly use stainless steel, a nickel-titanium alloy, platinum, iridium, tungsten or a combination of two or more of these materials.

As materials for composing the non-metal member, it is possible to singly use carbon, polyamide, polyethylene terephthalate, polybutylene terephthalate or combination containing two or more of these substances.

It is preferable to compose the coil 3 of a radiopaque material such as tungsten, platinum, iridium or an alloy containing these metals. As will be made later in detail in the description of the region 42, the front end of the coil 3 can be functioned as a radiopaque marker by making the winding pitch of only the front end of the coil 3 small in the neighborhood (region 42) of the front end of the body 2.

The coil 3 may be flat in its cross-sectional shape, namely, ribbon-shaped (belt-shaped) instead of the circular shape shown in FIGS. 2 through 5.

In the case where the coil 3 is circular in its cross-sectional shape, its diameter is favorably 10–100 $\mu$m and more favorably 30–60 $\mu$m.

In the case where the coil 3 is ribbon-shaped in its cross-sectional shape, its width is favorably 0.1–1.0 mm and its thickness is favorably 0.04–0.05 mm.

The coil 3 having the above-described shape and dimension has a sufficient reinforcing effect although it is comparatively thin. Therefore, the body 2 can have a small diameter or can be thin by providing it with the coil 3 having the above-described shape and dimension.

The front end of the coil 3 is spaced rearward at a predetermined interval from the front end of the body 2, namely, the front end of the first region 4. That is, at the front side of the first region 4, there is formed the region 41 in which the coil 3 is not present. The front end of the region 41 is tapered. Therefore, it is possible to improve operability of inserting the catheter 1 into the blood vessel and selectivity of a blood vessel from among branching blood vessels.

The length of the region 41 is favorably 0.5–5 mm and more favorably 1–2 mm.

There is a variation in the winding pitch of a part of the coil 3 disposed in the first region 4 which includes a part extending from the front end of the catheter 1 to a position 5 mm apart from the front end thereof. That is, the winding pitch of the coil in the first region 4 becomes gradually shorter forward from the region 45 toward the region 42 in the order of the region 45, the region 44, the region 43, and the region 42. The winding pitch of the part of the coil 3 disposed in the first region 4 may become gradually smaller continuously or stepwise. The winding pitch of the coil 3 in the first region 4 is preferably 30–300 $\mu$m. It is preferable that the relationship between the winding pitch (S1) of the coil 3 at the rear end of the first region 4 and the winding pitch (E) of the coil 3 at its front end is $E \leq \frac{3}{4} \times S1$. It is also preferable that the winding pitch (M1) of the coil 3 at the middle point between the rear end of the first region 4 and the front end of the coil 3 is $0.7 \times (S1+E)/2 \leq M1 \leq 1.3 \times (S1+E)/2$.

The winding pitch of the coil 3 disposed between the front end of the catheter 1 and at a position within 5 mm from the front end of the catheter 1 is favorably 30–300 $\mu$m, and more favorably 100–200 $\mu$m. It is preferable that the relationship between the winding pitch (S2) of the coil 3 at a position 5 mm apart from the front end of the catheter 1 and the winding pitch (E) of the coil 3 at its front end is $E \leq \frac{3}{4} \times S2$. It is also preferable that the winding pitch (M2) of the coil 3 at the middle point between the position 5 mm apart from the front end of the catheter 1 and the front end of the coil 3 is preferably $0.7 \times (S2+E)/2 \leq M2 \leq 1.3 \times (S2+E)/2$.

In the catheter 1 of the embodiment, the following relationship is established among a winding pitch a1 of the coil 3 in the region 42, a winding pitch a2 thereof in the region 43, a winding pitch a3 thereof in the region 44, and a winding pitch a4 thereof in the region 44: a4>a3>a2>a1. In each of the regions 42, 43, 44, and 45 of the first region 4, the coil 3 is wound with adjacent windings thereof not in close contact but with relatively short intervals provided between the adjacent windings thereof. In other words, even in the region 42 in which the coil 3 is wound at the shorter pitch than any of the regions 43, 44, and 45, the adjacent windings of the coil 3 are very close to each other but have the pitch a1 longer than zero therebetween. That is, adjacent windings of the coil 3 are spaced at very short pitches but do not contact each other with the gap left therebetween.

On the other hand, the winding pitch of the coil 3 in the second region 5 is longer than that of the coil 3 in the first region 4. That is, the winding pitch b of the coil 3 in the second region 5 is longer than any of the winding pitches a1, a2, a3, a4, and a5 in the first region 4. The winding pitch b of the coil 3 in the second region 5 is almost uniform (same pitch or almost same pitch in the entire length of the second region 5).

In the catheter 1, the winding pitch of the coil 3 in the first region 4 changes toward the front end of the catheter 1. Therefore, the first region 4 is more bendable (low in rigidity) and flexible than the first region 4 in which the coil 3 is wound at almost regular pitches. It is conceivable that as the winding pitch of the coil 3 becomes shorter, the rigidity of the catheter 1 (body 2) having the wound coil 3 becomes increasingly high. But by changing the winding pitch of the coil 3 in the first region 4, a plurality of regions having different physical properties (rigidity, hardness) are formed in the coil-embedded body 2 along the longitudinal direction thereof. Thereby the rigidity of the first region 4 the winding pitch becomes shorter toward the front end of the catheter is lower than that of the first region 4 having the coil 3 wound at regular pitches. Accordingly, although the winding pitch of the coil 3 in the first region 4 is shorter than that of the coil 3 in the second region 5, the catheter 1 has a lower rigidity in the first region 4 than in the second region 5.

By disposing the coil 3 wound at relatively shorter pitches in the first region 4, the catheter 1 has a high kink resistance and a high pressure resistance in the first region 4.

Because the coil 3 extends from the first region 4 to the second region 5, there is no sudden change in the rigidity (flexural rigidity) of the catheter 1 at the boundary between the first region 4 and the second region 5. Thus, there is no fear that the catheter 1 is kinked or bent at the boundary between the second region 5 having the higher rigidity and the first region 4 having the lower rigidity.

As apparent from the above description, the rigidity of the catheter 1 is lower in the first region 4 than in the second region 5. That is, in the second region 5, the catheter 1 has a sufficient rigidity and excellent pressing performance, whereas in the first region 4 which is located at the front end of the catheter 1, the catheter 1 is flexible and bendable, has excellent follow-up performance, and in addition a high kink resistance and pressure resistance.

The front end of the coil 3 disposed in the region 42 of the first region 4 is wound at very short pitches a1. Therefore, the front end of the coil 3 can be composed of the radiopaque marker to allow the front end thereof to be visible under the presence of an X-ray. Thereby it is possible to function the front end of the coil 3 as the radiopaque marker for recognizing the position of the catheter 1 under the presence of the X-ray.

In the catheter 1 having the above-described construction, it is unnecessary to mount the radiopaque marker separate from the coil 3 and having a high rigidity on the first region 4 low in rigidity (flexibility) and bendable to recognize the catheter 1 under the presence of the X-ray. Accordingly, unlike the conventional catheter, the bendability (flexibility) of the catheter 1 having the above-described construction does not deteriorate because it is unnecessary to mount the radiopaque marker having a high rigidity on the first region 4. Thus, the catheter 1 has superior follow-up performance and visibility of the catheter 1 under the presence of the X-ray.

The manner of winding the coil 3 in the first region 4 is not limited to that of the embodiment, provided that its winding pitch decreases continuously or stepwise. For example, in each of the regions 42, 43, 44, and 45, instead of setting the winding pitch of the coil 3 uniformly, but it is possible to set the winding pitch thereof gradually shorter toward the front end of the catheter 1. Otherwise, it is possible to set the winding pitch of the coil 3 continuously (stepless) shorter from the rear end of the first region 4 toward its front end. In the embodiment, in the first region 4 having the regions 42, 43, 44, and 45, the winding pitch of the coil 3 is varied at three or more steps, namely, at four steps, but may be varied at two steps, three steps or five or more steps.

The winding pitch of the coil 3 in the second region 5 is not necessarily uniform in the entire range thereof, but may be almost uniform as compared with the change of the winding pitch in the first region 4. That is, the pitch in the second region 5 is uniform in the entire range thereof or slightly varied in the longitudinal direction of the catheter 1. In other words, so long as the second region 5 has a higher rigidity than the first region 4, a slight change of the winding pitch of the coil 3 is permitted in the second region 5 in the longitudinal direction of the catheter 1. However, if there is a sudden change in the winding pitch of the coil 3 in the longitudinal direction of the catheter 1, a plurality of regions having different physical properties (rigidity) are formed in the second region 5. Consequently, there is a possibility that the second region 5 has a lower rigidity than the first region 4. In this case, it is difficult to transmit a pressing force applied to the rear end of the catheter 1 to the first region 4. Accordingly, the degree of the change of the winding pitch of the coil 3 in the second region 5 is required to be lower than the degree of the change of the winding pitch thereof in the first region 4. The part of the coil 3 disposed in the first region 4 is integral with the part of the coil 3 disposed in the second region 5.

As shown in FIG. 2, in the catheter 1 of the embodiment, the third region 6 has a part 61 positioned at the front end thereof, a part 62 positioned nearer to the rear end of the catheter 1 than the part 61 and adjacent to the part 61, and a part 63 positioned nearer to the rear end of the catheter than the part 62 and adjacent to the part 62.

The winding pitch of the coil 3 in the third region 6 becomes gradually longer toward the rear end of the catheter 1 in order of the parts 61, 62, and 63. That is, the following relationship is established among a winding pitch c1 of the coil 3 in the part 61, a winding pitch c2 thereof in the part 62, a winding pitch c3 thereof in the part 63: c1<c2<c3.

The winding pitch of the coil 3 in the third region 6 is longer than the winding pitch thereof in the second region 5. That is, any of the winding pitches c1, c2, and c3 of the coil 3 in the third region 6 are longer than the winding pitch b of the coil 3 in the second region 5.

Thereby the winding direction of the coil 3 in the third region 6 is closer to the axial (longitudinal) direction of the catheter 1 than that of the coil 3 in the second region 5. Thus, the coil 3 disposed in the third region 6 allows the catheter 1 to have a higher rigidity. Accordingly, the rigidity of the catheter 1 becomes lower in order of the third region 6, the second region 5, and the first region 4.

The rigidity of the third region 6 is gradually increased by making the winding pitch of the coil 3 in the third region 6 gradually longer (continuously or stepwise) toward the rear end of the catheter 1. In other words, the rigidity of the third region 6 decreases gradually toward the front end of the catheter 1. By varying the winding pitch of the coil 3 in this manner, it is possible to decrease the rigidity of the catheter 1 continuously toward its front end.

In the catheter 1, the second region 5 and the third region 6 have a sufficient degree of rigidity and high pressing performance. Further, the first region 4 has superior follow-up performance and safety and in addition high pressure resistance and kink resistance. Furthermore, because the coil 3 extends in the first region 4, the second region 5, and the third region 6, there is no sudden change in the rigidity of the catheter 1 at the boundary between the first region 4 and the second region 5 and the boundary between the second region 5 and the third region 6. Thus, there is no fear that the boundaries are kinked or bent.

The part of the coil 3 disposed in the first region 4 is integral with the part of the coil 3 disposed in the second region 5 and third region 6.

As described above, according to the present invention, it is possible to decrease the rigidity (mechanical property) of the catheter 1 gradually toward the front end of the catheter 1 by merely varying the winding pitch of the coil 3 in the longitudinal direction of the catheter 1.

The length of each of the first region 4, the second region 5, and the third region 6 is varied according to the use of the catheter 1 and not limited to a specific length. The following ranges are favorable for a micro-catheter for administering or injecting various medicines, a thrombus substance or a contrast medium to a desired portion in the internal organs such as brain or belly(for example, liver).

That is, the length of the first region 4 is favorably 1–30 mm and more favorably 2–10 mm. The length of the second region 5 is favorably 50–500 mm and more favorably 100–300 mm. The length of the third region 6 is favorably 500–1500 mm and more favorably 700–1000 mm. In particular, in the case where the first region 4 is located in the length not less than 5 mm from the front end of the body 2, the catheter 1 is sufficiently flexible (low in rigidity) in the first region 4. Thus, in advancing the catheter 1 to a desired portion of a blood vessel (lumen), the first region 4 can flex sufficiently along the curvature of the guide wire 9 (see FIG. 1). That is, it is possible to improve the follow-up performance of the catheter 1.

The winding pitch of the coil 3 in the first region 4 is not limited to a specific dimension. The winding pitch a1 of the coil 3 at its front end (in the embodiment, the winding pitch in the region 42) in the first region 4 is favorably 30–200 $\mu$m and more favorably 50–100 $\mu$m. The winding pitch a4 of the coil 3 at its rear end (in the embodiment, the winding pitch in the region 45) in the first region 4 is favorably 50–300 $\mu$m and more favorably 100–200 $\mu$m. By varying the winding pitch of the coil 3 within this range toward the front end of the first region 4, the catheter 1 is sufficiently flexible (low in rigidity) in the first region 4. Thus, in advancing the catheter 1 to a desired portion of a blood vessel (lumen), the first region 4 can flex sufficiently along the curvature of the guide wire 9 (see FIG. 1). That is, it is possible to improve the follow-up performance of the catheter 1.

The winding pitch of the coil 3 disposed in the second region 5 is favorably 100–500 $\mu$m and more favorably 150–250 $\mu$m. The winding pitch of the coil 3 disposed in the third region 6 is favorably 200–1000 $\mu$m and more favorably 250–400 $\mu$m.

In the case where the winding pitch of the coil 3 in each of the first region 4, the second region 5, and the third region 6 is in the above-described range, it is possible to impart a proper rigidity to the body 2 and allow the catheter 1 to have preferable flexibility (follow-up performance), kink resistance, and pressure resistance in the first region 4.

The position of the front end of the coil 3 disposed in the region 42 can be easily recognized under the presence of the X-ray by setting the winding pitch of the coil 3 to the above-described range in the region 42 and composing the coil 3 of the radiopaque material.

As the material of the body 2, the following flexible materials are used: polyolefins such as polypropylene, ethylene-vinyl acetate copolymer; polyamide, polyesters such as polyamide, polyethylene terephthalate (PET), polybutylene terephthalate (PBT); fluorocarbon resins such as polytetrafluoroethylene, ethylene-tetrafluoroethylene copolymer; polyurethane, polyvinyl chloride, polystyrene resin, flexible resins such as polyamide elastomer, polyurethane elastomer, polystyrene elastomer, polyester elastomer, fluoro-elastomer; rubber materials such as silicone rubber, latex rubber; and combinations of two or more of these substances.

The body 2 has a rear section and a front section disposed forward from the rear section. It is preferable that the front section has a lower rigidity than the rear section. To do so, the rear section of the body 2 is composed of a material having a comparatively high rigidity and the front section is composed of a material having a comparatively low rigidity by selecting them from among the above-described materials for the body 2. It is particularly preferable that the front section having a low rigidity is formed throughout the first region 4. Thereby it is possible to compose the first region 4 more bendably and flexibly (low rigidity) and allow the catheter 1 to have improved follow-up performance.

Owing to this construction and the change of the winding pitch of the coil 3, it is possible to decrease the rigidity of the catheter 1 continuously toward the front end thereof. In other words, even though the first region 4 is so constructed that it has a low rigidity in the first region 4, the catheter 1 has high kink resistance and pressure resistance. This is because the winding pitch of the coil 3 in the first region 4 is relatively low. Accordingly, the catheter 1 thus constructed displays high pressing performance and torque transmission performance at the rear side of the catheter 1 and has superior flexibility and follow-up performance and in addition high kink resistance and pressure resistance at the front side thereof.

In the embodiment, the body 2 has an inner layer 7 and an outer layer 8. The coil 3 is interposed between the inner layer 7 and the outer layer 8.

The outer layer 8 is provided on the outer side of the coil 3 to cover the coil 3. As shown in FIGS. 2 and 3, a part of the outer layer 8 (inner peripheral part of the outer layer 8) in its thickness direction is in penetration between adjacent windings of the coil 3 in the first region 4, the second region 5, and the third region 6. Owing to the penetration of a part of the coil 3 between the adjacent windings of the coil 3 and the variation of the winding pitch of the coil 3, in the first region 4, the outer layer 8 has a plurality of regions having different physical properties (rigidity, hardness) in its longitudinal direction. Thus, the first region 4 is bendable (low in rigidity) and flexible. Accordingly, although the winding pitch of the coil 3 in the first region 4 is shorter than the winding pitch thereof in the second region 5, the catheter 1 is so constructed that the rigidity thereof is lower in the first region 4 than in the second region 5.

As the material of the outer layer 8, the following flexible materials are used: polyolefins such as polypropylene, ethylene-vinyl acetate copolymer; polyamide, polyesters such as polyethylene terephthalate (PET), polybutylene terephthalate (PBT); fluorocarbon resins such as polytetrafluoroethylene, ethylene-tetrafluoroethylene copolymer; polyurethane, polyvinyl chloride, polystyrene resin, flexible resins such as polyamide elastomer, polyurethane elastomer, polystyrene elastomer, polyester elastomer, fluoro-elastomer; rubber materials such as silicone rubber, latex rubber; and combinations of two or more of these substances.

In the embodiment, the outer layer 8 has a first part 81 disposed at the front end of the catheter 1, a second part 82 disposed nearer to the rear end of the catheter 1 than the first part 81, a third part 83 disposed nearer to the rear end of the catheter 1 than the second part 82, a fourth part 84 disposed nearer to the rear end of the catheter 1 than the third part 83, a fifth part 85 disposed nearer to the rear end of the catheter 1 than the fourth part 84. Thereby the outer layer 8 is divided into a rear section consisting of the third part 83, the fourth part 84, and the fifth part 85; and a front section consisting of the first part 81 and the second part 82 and disposed nearer to the front end of the catheter 1 than the rear section.

These parts are so arranged that the hardnesses (rigidity) of materials composing these parts decrease continuously or stepwise from the rear end of the outer layer 8 to its front end, namely, in the order of the fifth part 85, the fourth part 84, the third part 83, the second part 82, and the first part 81. Thereby the front section (section consisting of the first part 81 and the second part 82) of the outer layer 8 has a lower rigidity than the rear section (section consisting of the fifth part 85, the fourth part 84, and the third part 83) of the outer layer 8. As shown in FIGS. 2 and 3, the front section (section consisting of the first part 81 and the second part 82) of the outer layer 8 having the lower rigidity extends throughout the first region 4. Thereby it is possible to compose the first region 4 bendably and flexibly (low in rigidity) and allow the catheter 1 to have improved follow-up performance.

Owing to the construction that the front section of the outer layer 8 has a lower rigidity than the rear section thereof and the change of the winding pitch of the coil 3, it is possible to decrease the rigidity of the catheter 1 continuously toward the front end thereof. In other words, even though the outer layer 8 is so constructed that it has a low rigidity in the first region 4, the catheter 1 has high kink resistance and pressure resistance. This is because the winding pitch of the coil 3 in the first region 4 is relatively low. Accordingly, the catheter 1 thus constructed displays high pressing performance and improved torque transmission performance at the rear side of the catheter 1 and displays superior flexibility and follow-up performance and in addition high kink resistance and pressure resistance at the front side thereof.

As shown in FIGS. 2 and 3, the front end and rear end of each of the first part 81, the second part 82, the third part 83, the fourth part 84, and the fifth part 85 are not coincident with the front end and rear end of each of the first region 5, the second region 5, and the third region 6 in the longitudinal direction of the catheter 1. This construction allows the rigidity of the catheter 1 to decrease continuously toward the front end of the catheter 1. Accordingly, the bending rigidities of the respective regions of the body 2 balance favorably with each other. In particular, the construction allows the rear side of the body 2 to have a sufficient rigidity and thus allows it to display high pressing performance and torque transmission performance and also allows the front side of the body 2, particularly the first region 4 to display high follow-up performance, kink resistance, and safety.

The hardness of the front section of the outer layer 8, namely, the hardness of each of the first and second parts 81 and 82 of the outer layer 8 is not limited to a specific value. However, the Shore D hardness thereof is favorably in the range of 10 to 60 and more favorably in the range of 20–50.

The hardness of the rear section of the outer layer 8, namely, the hardness of each of the fifth, fourth, and third parts 85, 84, and 83 of the outer layer 8 is not limited to a specific value. However, the Shore D hardness thereof is favorably in the range of 60 to 80 and more favorably in the range of 62–75. By setting the hardness thereof to the above-described range, the catheter 1 has the pressing performance, the torque transmission performance, the follow-up performance, and the kink resistance balancing well with each other.

The thickness of the outer layer 8 is not limited to a specific dimension. The thickness of the outer layer 8 is favorably in the range of 0.05 to 0.15 mm and more favorably in the range of 0.06 to 0.12 mm. If the thickness of the outer layer 8 is smaller than the lower limit value, there may be a case in which the pressing performance and the torque transmission performance are not displayed sufficiently. On the other hand, the outer layer 8 having a thickness larger than the upper limit value has a disadvantage in making the diameter of the body 2 small.

As shown in FIG. 2, in the embodiment, the outer layer 8 is so constructed that its thickness is almost uniform from the rear end of the body 2 to its front end, but may decrease gradually toward the front end of the body 2. Thereby the rigidity (bending rigidity) of the catheter 1 decrease continuously. Therefore, the body 2 has improved follow-up performance and kink resistance.

The length of each of the first part 81, the second part 82, the third part 83, the fourth part 84, and the fifth part 85 is varied according to the kind of the catheter and not limited to a specific length. The following ranges are favorable for a micro-catheter for administering or injecting various medicines, a thrombus substance or a contrast medium to a desired portion of the internal organs such as brain or belly (for example, liver).

The length of the first part 81 of the outer layer 8 is favorably in the range of 5 to 100 mm. The length of the second part 82 of the outer layer 8 is favorably in the range of 30 to 200 mm. The length of the third part 83 of the outer layer 8 is favorably in the range of 30 to 100 mm. The length of the fourth part 84 of the outer layer 8 is favorably in the range of 30 to 100 mm. The length of the fifth part 85 of the outer layer 8 is favorably in the range of 300 to 1500 mm.

The construction of the outer layer 8 is not limited to that of the embodiment. For example, the outer layer 8 may be formed of the same material and may have the same rigidity (hardness) from the front end thereof 2 to its rear end.

It is preferable that the outer layer has the front section and the rear section, that the front section is composed of a polyester elastomer, and that the rear section is composed of a polyurethane elastomer having a higher rigidity than the polyester elastomer.

By composing the outer layer thus, while the operability of the catheter such as the pressing performance, the torque transmission performance, the follow-up performance, and kink resistance is secured, a hydrophilic polymeric substance can be preferably imparted to the outer surface of the catheter. The front section of the outer layer is formed from the front end of the body 2 to a position spaced at a certain interval from the front end of the body 2. The rear section of the outer layer is formed continuously with the front section and terminates at a rear end 21 of the body 2.

It is preferable that the front section of the outer layer has a plurality of parts and that the hardness (rigidity) of a material composing each part of the front section of the outer layer decreases continuously or stepwise from the rear end of the front section toward its front end. It is also preferable that the hardness (rigidity) of the entirety of the outer layer 8 decreases continuously or stepwise from the rear end thereof toward the front end thereof.

The catheter 1 in which the outer layer is composed as described above allows the bending rigidities of the respective regions of the body 2 to balance favorably with each other. In particular, it is possible to allow the second region 5 to have a sufficient rigidity and thus display high pressing performance and torque transmission performance and allow the first region 4 to have high follow-up performance, kink resistance, and safety.

It is preferable that the front section of the outer layer 8 is composed of the polyester elastomer and that rear section of the outer layer 8 is composed of the polyurethane elastomer.

The hardness of the polyester elastomer is not limited to a specific value. However, the Shore D hardness thereof is favorably in the range of 25 to 60 and more favorably in the range of 28–55. The polyurethane elastomer for the rear section of the outer layer has a higher hardness than the polyester elastomer for the first region. The hardness of the polyurethane elastomer is not limited to a specific value. The Shore D hardness thereof is favorably in the range of 60 to 80 and more favorably in the range of 62 to 75.

By setting the hardness of the polyester elastomer and the polyurethane elastomer to the above-described range, the catheter 1 has pressing performance, torque transmission performance, follow-up performance, and kink resistance balancing well with each other.

As the polyester elastomer composing the front section of the outer layer, it is possible to use a copolymer (random copolymer, block copolymer and the like) containing a hard segment and a soft segment.

As the hard segment, polybutylene terephthalate, polyethylene terephthalate, dihidroxyparaquarterphenyl can be used. The polybutylene terephthalate is more favorable than the other substances.

As the soft segment, it is possible to use polytetramethylene terephthalate, polytetramethylene ether glycol, poly (1,2-propylene oxide) glycol, poly (ethylene oxide) glycol, and polycaprolactam. The polytetramethylene terephthalate and the polytetramethylene ether glycol are more favorable than the other substances.

As the polyurethane elastomer composing the rear section of the outer layer, it is possible to use a copolymer (random copolymer, block copolymer and the like) containing a hard segment and a soft segment.

As the hard segment, polymers containing diisocyanate and short-chain glycol can be used.

As the diisocyanate, the following substances can be used: 4,4'-diphenylmethanediisocyanate, 2,4'-toluenediisocyanate, 2,6-toluenediisocyanate, 1,6-hexamethylenediisocyanate, 3,3'-dimethyldiphenyl-4,4'-diisocyanate, 1,5'-naphthalanediisocyanate. Of these substances, the 4,4'-diphenylmethanediisocyanate is more favorable than the other substances.

As the short-chain glycol, it is possible to use 1,4-butanediol, ethylene glycol; 1,3-propylene glycol; 1,3-butylene glycol; 1,4-butylene glycol; 1,6-hexyl glycol; 1,4-dimethylol benzene; and bisphenol A. Of these short-chain glycols, the 1,4-butanediol is more favorable than the other short-chain glycols.

As the soft segment, it is possible to use polymers containing diisocyanate and long-chain glycol or use only the long-chain glycol.

As the diisocyanate, it is possible to use the same substances as those which can be used for the hard segment. Of those substances, the 4,4'-diphenylmethanediisocyanate is more favorable than the other substances.

As the long-chain glycols, the following substances can be used: polytetramethylene ether glycol, poly (oxypropylene) glycol, poly (ethylene adipate) glycol, poly (butylene-1,4-adipate) glycol, poly (ethylene-1,4-adipate) glycol, poly (hexanediol-1,6-carbonate) glycol, polycaprolactam glycol poly (diethylene glycol adipate) glycol, and (hexanediol-1,6-carbonate) glycol. Of these substances, the polytetramethylene ether glycol is more favorable than the other glycols.

By composing the outer layer 8 of the polyester elastomer and the polyurethane elastomer, it is easy to impart a hydrophilic polymeric substance which will be described later to the outer surface of the outer layer 8 and hold the hydrophilic polymeric substance thereon.

The thickness of the outer layer 8 is not limited to a specific value. The thickness of the outer layer 8 is favorably in the range of 0.05 to 0.15 mm and more favorably in the range of 0.06 to 0.12 mm. If the thickness of the outer layer 8 is smaller than the lower limit value, there may be a case in which the pressing performance and the torque transmission performance are not displayed sufficiently. On the other hand, the outer layer 8 having a thickness larger than the upper limit value is at a disadvantage in making the diameter of the body 2 small.

As shown in FIG. 2, in the embodiment, the thickness of the outer layer 8 is almost uniform from the rear end of the body 2 to its front end, but may decrease gradually toward the front end of the body 2. Thereby the rigidity (bending rigidity) of the body 2 decrease continuously. Therefore, the body has improved follow-up performance and kink resistance.

The inner layer 7 covers the inner side of the coil 3. The inner layer 7 serves as the core for disposing the coil 3 in the body 2 and forms a lumen 21 therein.

As the material for the inner layer 7, it is possible to use a material similar to that for the outer layer 8. It is preferable to compose the inner layer 7 of a material having a low friction coefficient to allow the inner surface of the inner layer 7 to have a low degree of friction. Thereby it is possible to reduce the sliding-contact resistance of the inner layer 7 to the guide wire 9 (see FIG. 1) inserted into the lumen 21. Thus, it is possible to easily and smoothly perform an operation of inserting the catheter 1 into a blood vessel along the guide wire precedent to the front end of the catheter 1 and an operation of pulling out the guide wire from the catheter 1.

Any material having a low friction coefficient can be used for the inner layer 7, so long as it can reduce the friction of the inner surface of the inner layer 7. For example, it is possible to use fluorocarbon resin, nylon 66, polyether ether ketone, and high-density polyethylene. The fluorocarbon resin is more favorable than the other substances.

As the fluorocarbon resin, the following substances can be used: polytetrafluoroethylene, polyvinylidene fluoride, ethylene tetrafluoroethylene, and perfluoroalcoxy resin. The polytetrafluoroethylene is more favorable than the other substances.

The thickness of the inner layer 7 is not limited to a specific value, but is favorably less than 50 $\mu$m and more favorably less than 40 $\mu$m. The inner layer 7 having a thickness larger than the upper limit value is at a disadvantage in making the diameter of the body 2 small.

As shown in FIGS. 2 and 3, a part of the inner layer 7 (outer peripheral part of the inner layer 7) in its thickness direction is in penetration between adjacent windings of the coil 3 in the first region 4, the second region 5, and the third region 6. Owing to the penetration of a part of the coil 3 between the adjacent windings of the coil 3 and the variation of the winding pitch of the coil 3, in the first region 4, the inner layer 7 has a plurality of regions having different physical properties (rigidity, hardness) in its longitudinal direction. Thus, the first region 4 is bendable (low in rigidity) and flexible. Accordingly, although the winding pitch of the coil 3 in the first region 4 is shorter than the winding pitch thereof in the second region 5, the catheter 1 is so constructed that the rigidity thereof is lower in the first region 4 than in the second region 5.

In the case where the inner layer 7 has a higher rigidity than the outer layer 8 in the first region 4, the rigidity of the inner layer 7 having the higher rigidity acts mainly in the first region 4 as the entire rigidity of the catheter 1. But the inner layer 7 is in penetration between the windings of the coil 3. Thus, with the change of the winding pitch of the coil 3, the inner layer 7 is bendable and flexible (low in rigidity). Thereby the rigidity of the inner layer 7 in the first region 4 can be preferably reduced. Thus, the catheter 1 has a reduced rigidity in the first region 4 and is thus bendable.

In the embodiment, the coil 3 is wound on the periphery of the inner layer 7 by cutting the coil 3 into the periphery of the inner layer 7. Accordingly, the periphery of the inner layer 7 is compressed by the wound coil 3. It is possible to preferably penetrate the inner layer 7 between the adjacent windings of the coil 3 by winding the coil 3 in this manner.

For example, the catheter main body 2 that mentioned above can manufacture it by the method that expresses below.

Initially, the inner layer 7 is mounted on the periphery of a mandrel (core material). The inner layer 7 can be formed by hollow extrusion molding, wire-coating molding or applying (or immersing) a solution containing a material for the inner layer 7 to the periphery of the core material and drying the solution.

Then, a wire, namely, the coil 3 is wound spirally on the periphery of the inner layer 7 by varying the winding pitch of the coil 3 in the longitudinal direction of the mandrel to mount the coil 3 on the periphery of the inner layer 7. In the winding operation, the wire is wound onto the periphery of the inner layer 7, with a predetermined winding tensile force applied to the wire. Thereby the inner layer 7 is compressed by the wound coil 3 and penetrates between the adjacent windings of the coil 3.

Then, the first part 81, the second part 82, the third part 83, the fourth part 84, and the fifth part 85 of the outer layer 8 are prepared as hollow tubular bodies by hollow extrusion molding more favorable than the wire-coating molding or wire-coating molding. The hardness, thickness, and length of each of the first part 81, the second part 82, the third part 83, the fourth part 84, and the fifth part 85 of the outer layer 8 are set to a predetermined value, respectively.

Then, the first part 81, the second part 82, the third part 83, the fourth part 84, and the fifth part 85 of the outer layer 8 are applied to the core material on which the inner layer 7 and the coil 3 have been mounted in a predetermined order.

A heat-shrinkable tube is applied to the first part 81, the second part 82, the third part 83, the fourth part 84, and the fifth part 85 of the outer layer 8. Then, the heat-shrinkable tube is heated to thermally shrink it. The heat-shrinkable tube preferable consists of fluorocarbon resin.

Thereby the material composing each of the first part 81, the second part 82, the third part 83, the fourth part 84, and the fifth part 85 of the outer layer 8 melts at the boundary between the first part 81 and the second part 82, between the second part 82 and the third part 83, between the third part 83 and the fourth part 84, and between the fourth part 84 and the fifth part 85. Consequently, the first part 81, the second part 82, the third part 83, the fourth part 84, and the fifth part 85 of the outer layer 8 become integral with each other. At the same time, the melted first, second, third, fourth, and fifth parts 81, 82, 83, 84, and 85 of the outer layer 8 flow (penetrate) into the gap between the adjacent windings of the coil 3 and adhere to the periphery of the inner layer 7. In this manner, the inner layer 7 and the outer layer 8 become integral with each other.

Then, the heat-shrinkable tube is removed from the first, second, third, fourth, and fifth parts 81, 82, 83, 84, and 85 of the outer layer 8. Then, the end (unnecessary portion of the body 2) of the semi-finished product is cut off. Then, the mandrel is pulled out from the semi-finished product before or after the cut-off operation.

As other methods of forming the outer layer 8, extrusion molding method or dipping method may be used to apply a material for the outer layer 8 to the outer side of the coil 3 and the inner layer 7.

A hydrophilic polymeric substance which will be described later is imparted to a predetermined portion of the outer surface of the catheter body 2 manufactured in this manner.

Thereafter, the front end of the body 2 is tapered and the hub 11 is mounted on its rear end to complete the manufacture of the catheter 1.

In this invention, the outside diameter of the front end of catheter 1 (catheter main body 2) is 1.5 mm or less, and are 1.0 mm or less desirably.

The outer diameter of the body 2 is not limited to a specific dimension. In the case where the catheter 1 is used as a micro-catheter for administering or injecting various medicines, a thrombus substance or a contrast medium to a desired portion of the internal organs (for example, liver) such as brain or belly, it is preferable to set the outer diameter of the body 2 to the range of 0.5 to 1.0 mm.

The outer diameter of the body 2 is not limited to the range of 0.5 to 1.0 mm in the case where the catheter of the present invention is not used as the micro-catheter.

According to the present invention, it is preferable to apply the hydrophilic polymeric substance to the outer surface of the front side of the outer layer 8. Thereby the outer surface of the body 2 displays lubricity when it contacts a aqueous liquid such as blood or physiologic saline. Thus the body has a decreased frictional and improved sliding performance. Consequently, the catheter 1 can be inserted into a blood vessel with high operability, namely, with high pressing performance, follow-up performance, kink resistance, and safety.

In the operation of inserting the catheter 1 into a blood vessel, it is necessary to hold the rear end of the body 2 in hand. The operability of inserting the catheter 1 into the blood vessel deteriorates if the rear end of the body 2 is slippery. In consideration of this, it is preferable to apply the hydrophilic polymeric substance not to the entirety of the body 2 in the longitudinal direction of the body 2 but to the region thereof except a predetermined range (for example, 150–500 mm) forward from the rear end of the body 2.

As the hydrophilic polymeric substance, the following natural or synthetic polymeric substances or derivatives of the polymeric substances can be used: a cellulose type polymeric substance (for example, hidroxypropyl cellulose), a polyethylene oxide polymeric substance (polyethylene glycol), a maleic anhydride type polymeric substances (for example, maleic anhydride copolymer such as methylvinyl ether maleic anhydride copolymer, copolymer of methyl vinyl ether and maleic anhydride ethyl ester, half-ester methyl vinyl ether-maleic anhydride copolymer neutralized, an acrylamide type polymeric substance (for example, polyacrylamide, dimethyl acrylamid-glycidyl methacrylate copolymer), and water-soluble nylon (for example, AQ-nylon P-70 manufactured by Toray Corp.). These polymeric substances are favorable because the friction coefficients thereof are stable. The maleic anhydride polymeric substance can be used more favorably than the other substances.

The derivatives of the polymeric substances are not limited to water-soluble ones but water-insoluble ones can be also used, provided that they contain the polymeric substances as their fundamental component and that they are able to contain water and the molecular chains thereof have degree of freedom.

To fix the hydrophilic polymeric substance to the outer surface of the body 2, it is preferable to covalently bond it to a reactive functional group present in the outer layer 8 or on the surface thereof or introduced thereinto. Thereby it is possible to allow the outer surface of the body 2 to keep good lubricity.

Any reactive functional groups present in the outer layer 8 or on the surface thereof or introduced thereinto can be used, provided that they react with the hydrophilic polymeric substance and combine with each other or cross-linked to each other and are then fixed to the outer surface of the body 2. As the reactive functional groups, the following substances can be used: diazonium group, azide group, isocyanate group, acid chloride group, acid anhydride group, imino carbonate group, amino group, carboxylic group, epoxy group, hydroxyl group, and aldehyde group. Of these groups, the isocyanate group, the amino group, the aldehyde group, and the epoxy group are more favorable than the other groups.

The present invention is not limited to the embodiment described above with reference to FIGS. 1 through 3.

Figure 4:
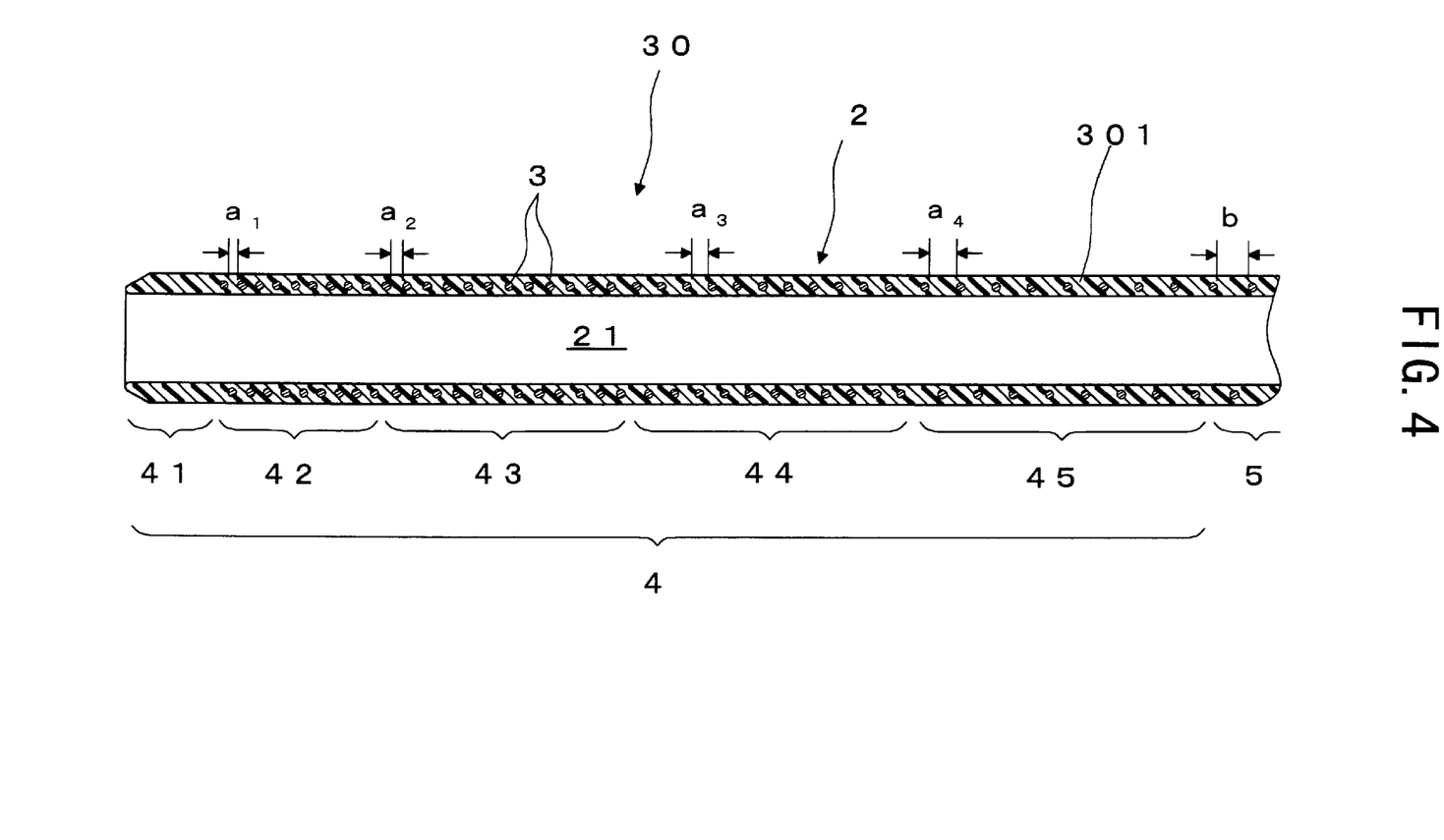
FIG. 4 is an enlarged sectional view showing a front side of a catheter according to another embodiment of the present invention.

For example, the tubular member (body 2) of the present invention is not limited to the construction, of the above-described embodiment, having the inner layer and the outer layer. As shown in FIG. 4, the body 2 (tubular member) may have a single layer 301 in which the coil 3 is embedded. FIG. 4 is an enlarged sectional view showing the front side of the catheter according to another embodiment of the present invention. The catheter 30 has an effect similar to that of the catheter 1 shown in FIGS. 1 through 3. The catheter 30 is different from that catheter 1 in only the above-described construction. In other points, the catheter 30 has the same construction as that of the catheter 1 described with reference to FIGS. 1 through 3.

Figure 5:
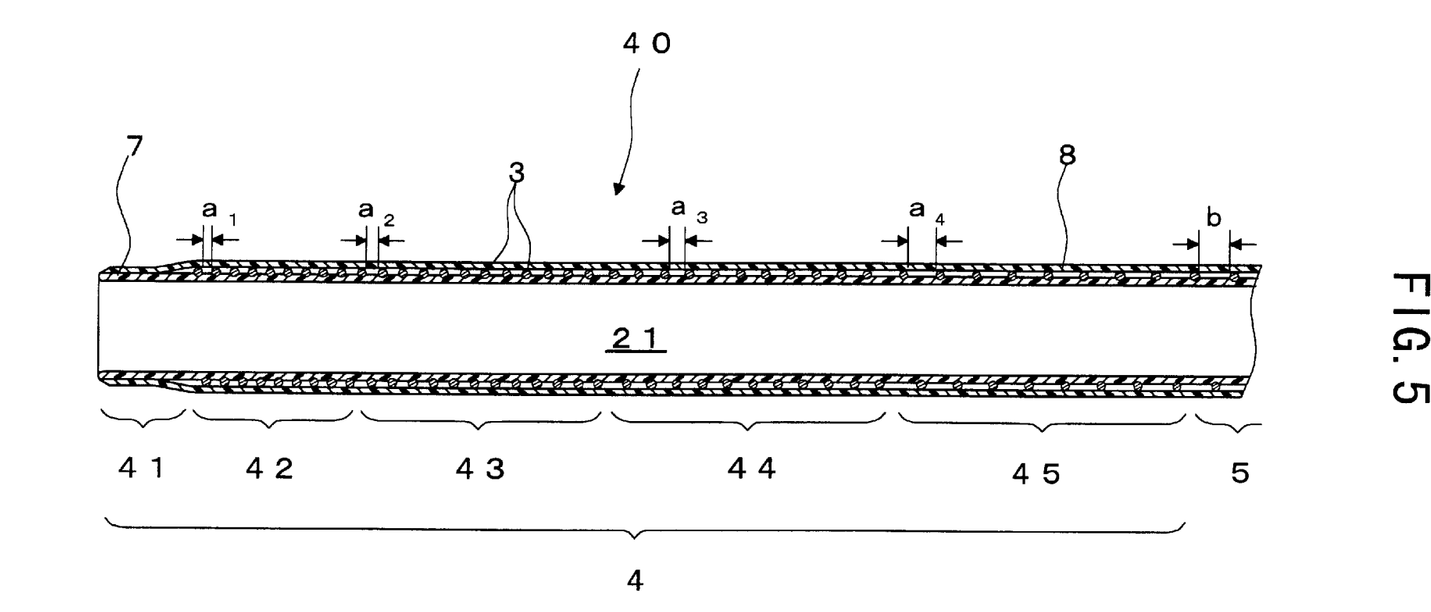
FIG. 5 is an enlarged sectional view showing a front side of a catheter according to still another embodiment of the present invention.

The construction of the tubular member (body 2) of the present invention is not limited to the construction having both the inner layer and the outer layer penetrating between adjacent windings of the coil 3. For example, as shown in FIG. 5, in a catheter 40, only the inner layer 7 penetrates between the adjacent windings of the coil 3, whereas the outer layer 8 provided on the outer side of the coil 3 does not penetrate between the adjacent windings of the coil 3. FIG. 5 is an enlarged sectional view showing the front side of the catheter according to another embodiment of the present invention. In the catheter 40, the outer layer 8 is liquid-tightly fixed to the periphery of the inner layer 7 with an adhesive agent or fused thereto in the region 41 disposed forward from the front end of the coil 3. The catheter 40 has also an effect similar to that of the catheter 1 shown in FIGS. 1 through 3. The catheter 40 is different from that catheter 1 in the above-described construction. In other points, the catheter 40 has the same construction as that of the catheter 1 described with reference to FIGS. 1 through 3. In addition, although not shown, the catheter of the present invention can be so constructed that only the outer layer 8 penetrates between the adjacent windings of the coil 3, whereas the inner layer 7 provided on the inner side of the coil 3 does not penetrate between the adjacent windings of the coil 3. Further, in addition to the inner layer 7 and the outer layer 8, the catheter may have one layer or two or more layers in addition to the inner layer 7 and the outer layer 8.

The catheter of the present invention is not limited to a specific application. It can be used as a guiding catheter; a contrast medium-introducing catheter; balloon catheters such as for PTCA, PTA, IABP; an ultrasonic wave catheter, an atherectomy catheter, a catheter for an endoscope, an indwelling catheter, a medicine-administering catheter, a micro-catheter (for embolization) for administering or injecting various medicines, a thrombus substance or a contrast medium to a desired portion of the internal organs (for example, liver) such as brain or belly. The catheter of the present invention is particularly advantageous because it can have a small diameter. The catheter having a small diameter can display the above-described effect efficiently.

Therefore, it is preferable to use the catheter of the present invention as the micro-catheter.

EXAMPLES

The examples of the present invention will be described below.

First Example

Polytetrafluoroethylene was applied to a mandrel (core material) made of silver-plated soft copper wire having a diameter of 0.65 mm by molding to form the inner layer 7 having a thickness of 35 $\mu$m on the peripheral surface of the mandrel.

The peripheral surface of the inner layer 7 was chemically treated with a solution consisting of a glicolic solvent and a solute of naphthalene complex of sodium salt.

Then, the core material coated with the inner layer 7 was cut to a length of 1500 mm.

A metal wire material of tungsten having a diameter of 50 $\mu$m was wound on the peripheral surface of the inner layer 7 by changing a winding pitch with a winding tensile force kept at 0.17 kg to form the coil 3.

The end of the metal wire material forming the coil 3 was cut off.

The outer layer 8 was formed on the peripheral surface of the inner layer 7 formed on the core material and on the coil 3 formed on the peripheral surface of the inner layer 7 as follows:

Initially, the first part 81, the second part 82, the third part 83, the fourth part 84, and the fifth part 85 of the outer layer 8 were formed as hollow tubular members by extrusion molding.

Then, the first part 81, the second part 82, the third part 83, the fourth part 84, and the fifth part 85 of the outer layer 8 were placed in a predetermined order on the core material on which the first layer 4 and the second layer 5 were formed.

Then, a heat-shrinkable tube (FEP) made of fluorocarbon resin was applied to the peripheral surface of the first part 81, the second part 82, the third part 83, the fourth part 84, and the fifth part 85 of the outer layer 8. Both ends of the heat-shrinkable tube was fixed with a stopper.

Then, the semi-finished product was passed into a heat tunnel for 10 minutes at 340° C. to fuse and connect the first part 81 and the second part 82 to each other, the second part 82 and the third part 83 to each other, the third part 83 and the fourth part 84 to each other, and the fourth part 84 and the fifth part 85 to each other.

Then, the heat-shrinkable tube was separated from the outer layer 8. Then, the part of the semi-finished product on which the outer layer 8 was not present was cut in a length of 200 mm from the end thereof. The mandrel was pulled out from the semi-finished product. In this manner, the body 2 having the first region 4 consisting of the region, 41, 42, 43, 44, and 45; the second region 5, and the third region 6 consisting of the parts 61, 62, and 63 was prepared.

The detail of each of the first region 4 (region, 41, 42, 43, 44, and 45), the second region 5, and the third region 6 (parts 61, 62, and 63), the first part 81, the second part 82, the third part 83, the fourth part 84, and the fifth part 85 of the outer layer 8 is as follows:

<First Region 4>

The length of the region 41: 1.0 mm

The length of the region 42: 0.9 mm

The winding pitch a1 of the coil 3 in the region 42: 95 $\mu$m

The length of the region 43: 1.3 mm

The winding pitch a2 of the coil 3 in the region 43: 110 $\mu$m

The length of the region 44: 1.5 mm

The winding pitch a3 of the coil 3 in the region 44: 140 $\mu$m

The length of the region 45: 1.5 mm

The winding pitch a4 of the coil 3 in the region 45: 190 $\mu$m

<Second Region 5>

The length: 50 mm

The winding pitch b of the coil 3 in the region 45: 220 $\mu$m

<Third Region 6>

The length of the part 61: 60 mm

The winding pitch c1 of the coil 3 in the part 61: 240 $\mu$m

The length of the part 62: 100 mm

The winding pitch c2 of the coil 3 in the part 62: 290 $\mu$m

The length of the part 63: 900 mm

The winding pitch c3 of the coil 3 in the part 63: 350 $\mu$m

<First Part 81 of Outer Layer>

Composing material: polyester elastomer (PELPRENE™ manufactured by Toyo Boseki Corp., Shore D hardness: 29)

Thickness: 0.08 mm

Length: 40 mm

<Second Part 82 of Outer layer>

Composing material: polyester elastomer (PELPRENE™ manufactured by Toyobo.co.,Ltd, Shore D hardness: 40)

Thickness: 0.08 mm

Length: 130 mm

<Third Part 83 of Outer layer>

Composing material: polyurethane elastomer (PELLETHANE™ manufactured by Dow Chemical Japan Corp., Shore D hardness: 65)

Thickness: 0.09 mm

Length: 30 mm

<Fourth Part 84 of Outer Layer>

Composing material: mixture of polyurethane elastomer (PELLETHANE™ manufactured by Dow Chemical Japan Corp., Shore D hardness: 65) and polyurethane (PELLETHANE™ manufactured by Dow Chemical Japan Corp., Shore D hardness: 75), with the polyurethane elastomer and the polyurethane mixed at the ratio of 2:1

Thickness: 0.09 mm

Length: 30 mm

<Fifth Part 85 of Outer Layer>

Composing material: polyurethane (PELLETHANE™ manufactured by Dow Chemical Japan Corp., Shore D hardness: 75)

Thickness: 0.1 mm

Length: 1000 mm

An operation of imparting a hydrophilic polymeric substance to the peripheral surface of the catheter body 2 prepared in the above-described manner was performed as follows:

As the pretreatment, a tetrahidrofuran (THF) solution of diphenylmethyl-diisocyanate adjusted to 5.3% was applied to the outer surface of the body 2. Then, the solution was dried for 30 minutes at the room temperature.

Then, treatment conducted twice was to apply the THF solution of a half-ester methyl vinyl ether-maleic anhydride copolymer neutralized adjusted to 1.65% to the peripheral surface of the body 2 and dry the solution for 30 minutes at the room temperature. Then, neutralization cleaning and pure water cleaning were performed, and the THF solution was dried.

The hub 11 was connected to the rear end of the body 2 to which the hydrophilic polymeric substance was applied to manufacture the catheter of the present invention.

(First Experiment)

To check the rigidity of the catheter of the first example, the following experiments were conducted:

A tubular member (first test example) was prepared by a method similar to that used to prepare the body 2 of the first example, except that the region 41 (region in which the coil 3 is not present) formed in the first example was not formed and that the coil 3 was wound from the front end of the inner layer 7 to its rear end.

That is, in the first test example, the winding pitch of the coil 3 was changed in the same manner as that of the first example. To compare the first test example with second through sixth test examples which will be described later, the coil 3 was wound over the whole length of the tubular member similarly to the second through sixth test examples.

For comparison, the following five tubular members of the second through sixth test examples were prepared:

The tubular member of the second test example was prepared in a manner similar to that used to prepare the body 2 of the first example, except that the coil 3 was wound over the whole length thereof at regular pitches of 95 μm.

The tubular member of the third test example was prepared in a manner similar to that used to prepare the body 2 of the first example, except that the coil 3 was wound over the whole length thereof at regular pitches of 200 μm.

The tubular member of the fourth test example was prepared in a manner similar to that used to prepare the body 2 of the first example, except that the coil 3 was wound over the whole length thereof at regular pitches of 290 μm.

The tubular member of the fifth test example was prepared in a manner similar to that used to prepare the body 2 of the first example, except that the coil 3 was wound over the whole length thereof at regular pitches of 350 μm.

The tubular member of the sixth test example was prepared in a manner similar to that used to prepare the body 2 of the first example, except that the coil 3 was wound over the whole length thereof at regular pitches of 400 μm.

With each of the first through sixth test examples fixed to a jig at a position 5 mm rearward from its front end, the maximum striking resistance value of each test example was measured by striking the front end of each test example against a plate made of silicone at a speed of 5 mm/min. A micro-load measuring device (MODEL-1305N manufactured by AIKOH ENGINEERING CO,.LTD was used for the measurement. The maximum striking resistance value of each test example was also measured by fixing each of the first through sixth test examples to the jig at the position 10 mm rearward from its front end. Table 1 shows the results.

TABLE 1

| | Maximum resistance value (gf, n = 1) 5 mm | Maximum resistance value (gf, n = 1) 10 mm |
|---|---|---|
| First test example | 39 | 24 |
| Second test example | 61 | 30 |
| Third test example | 46 | 26 |
| Fourth test example | 60 | 35 |
| Fifth test example | 63 | 33 |
| Sixth test example | 65 | 35 |

Table 1 indicates that when the winding pitch of the coil 3 was uniform over the whole length of each test example, the striking resistance was lowest when the winding pitch was in the neighborhood of 200 μm (third test example). Table 1 also indicates that as the winding pitch became shorter (second test example) than 200 μm or longer (fourth through sixth test examples) than 200 μm, the striking resistance became increasingly high. That is, it has been confirmed that when the winding pitch of the coil 3 was uniform over the whole length of each test example, the tubular member became most flexible (lowest in rigidity) in the neighborhood of 200 μm and that the tubular member became hard (high in rigidity) when the winding pitch was longer or shorter than 200 μm.

The winding pitch of the coil 3 of the first test example at its rear end was almost equal (220 μm) to that of the third test example at its rear end and became gradually shorter and was equal (95 μm) to that of the second test example at its front side. However, it has been confirmed that the maximum striking resistance of the first test example was lower than that of any of the second through sixth test examples. It has been also confirmed the maximum striking resistance of the first test example at the position of 5 mm rearward from its front end was much lower than that of each of the second through sixth test examples.

In the first test example, it has been confirmed that the first test example was more flexible (lower in rigidity) than any of the second through sixth test examples because in the first test example, the winding pitch of the coil 3 was changed from about 200 μm to 95 μm in the very short length (about 5 mm), whereas in the second through sixth test examples, the winding pitch was uniformly about 200 μm.

Accordingly, the catheter 1 of the first example had a lower rigidity and was thus more flexible in the first region 4 in which the winding pitch of the coil 3 was changed in the same manner as that of the first test example than in the second region 5 having the winding pitch similar to that of the third test example. That is, it has been confirmed the catheter could be formed flexibly by gradually reducing the winding pitch of the coil toward the front end of the catheter, although the coil was wound, with adjacent windings very close to each other in the predetermined length (for example, 5 mm) rearward from the front end of the catheter.

Table 1 also indicates that the catheter (body) had a higher rigidity in the third region 6 than in the second region 5 because the winding pitch (about 200 μm) which makes the rigidity (flexural rigidity) of the catheter minimum was selected in the second region 5 of the catheter 1 of the first example and the winding pitch of the coil 3 in the third region 6 was longer than that in the second region 5.

As apparent from the foregoing description, according to the present invention, by selecting and varying the winding pitch of the coil in each region of the catheter, the rigidity necessary for the catheter can be secured and high pressing performance is superior at its rear side, whereas flexibility (bendability) and follow-up performance are superior at its front side.

First Comparison Example

The catheter body was prepared in accordance with the procedure of the first example, except that the following substances were used as the first part 81 and the second part 82 of the outer layer of the body.
*First part 81 of outer layer: polyurethane elastomer (PELLETHANE™ manufactured by Dow Chemical Japan Corp., Shore D hardness: 30)
  Thickness: 0.08 mm, Length: 40 mm
*Second part 82 of outer layer: polyurethane elastomer (PELLETHANE™ manufactured by Dow Chemical Japan Corp., Shore D hardness: 40)
  Thickness: 0.08 mm, Length: 130 mm Second Comparison Example The catheter body 2 was prepared in accordance with the procedure of the first example, except that the following substances were used as the third part 83, the fourth part 84, and the fifth part 85 of the outer layer of the body.
*Third part 83 of outer layer: polyester elastomer (PELPRENE™ manufactured by Toyobo.co.,Ltd., Shore D hardness: 44)
  Thickness: 0.09 mm, Length: 30 mm
*Fourth part 84 of outer layer: polyester elastomer (PELPRENE™ manufactured by Toyobo.co.,Ltd., Shore D hardness: 57)
  Thickness: 0.09 mm, Length: 30 mm
*Fifth part 85 of outer layer: polyester elastomer (PELPRENE™ manufactured by Toyobo.co.,Ltd., Shore D hardness: 68)
  Thickness: 0.10 mm, Length: 1000 mm
(Second Experiment)

An operation of imparting a hydrophilic polymeric substance to the outer surface of the body 2 of the catheter of each of the first example, the first comparison example, and the second comparison example was performed.

The body 2 of each catheter was examined on the state of its outer surface and the lubricity-holding effect of the outer surface.

The operation of imparting the hydrophilic polymeric substance to the outer surface of the body 2 of each catheter was performed as follows:

As the pretreatment, the tetrahidrofuran (THF) solution of diphenylmethyl-diisocyanate adjusted to 5.3% was applied to the outer surface of the catheter body 2 of each of the first example, the first comparison example, and the second comparison example. Then, the solution was dried for 30 minutes at the room temperature.

Then, the treatment conducted twice was to apply the THF solution of the half-ester methyl vinyl ether-maleic anhydride copolymer neutralized (hydrophilic polymeric substance) adjusted to 1.65% to the peripheral surface of the body 2 of the catheter of each of the first example, the first comparison example, the second comparison example and dry the solution for 30 minutes at the room temperature. Then, neutralization cleaning and pure water cleaning were performed and water content was dried.

1. State of Outer Surface of Catheter Body 2

Change was admitted on neither the outer surface of the catheter body 2 of the first example nor the outer surface of the catheter body 2 of the second comparison example. On the other hand, the outer surface of the catheter body 2 of the first comparison example and in particular the outer surface of the parts 81 and 82 of the outer layer 8 were dissolved in the THF solution used in the operation of applying the hydrophilic polymeric substance to the outer surface of each catheter body 2. Thus, the catheter body 2 of the first comparison example cannot be used.

2. Lubricity-holding Effect of Outer Surface of Catheter Body 2

The lubricity-holding effect of the outer surface of catheter body 2 of each of the first example and the second comparison example was examined by conducting the following experiment.

The catheter body 2 of the first example and that of the second comparison example were repeatedly put into a commercially available angiography catheter manufactured by Terumo Kabushiki Kaisha and slid repeatedly longitudinally on the inner peripheral surface of the angiography catheter in which physiologic saline was filled, with the outer surface of both catheter bodies 2 wet with the physiologic saline.

The result was that the lubricity of the outer surface of the catheter body 2 of the first example was maintained when it was slid 60 times. On the other hand, the hydrophilic polymeric substance applied to the outer surface of the catheter body 2 of the second comparison example was separated therefrom in the region 85 when it was slid several times, and lubricity was lost.

As apparent from the foregoing description, in the catheter of the present invention, the winding pitch of the coil in the second region located at the rear side of the catheter is set relatively long, whereas the winding pitch of the coil in the first region located at the front end of the catheter is relatively short, with the winding pitch becoming gradually shorter toward the front end of the catheter. Therefore, the catheter has high operability such as pressing performance, follow-up performance, and kink resistance and in addition pressure resistance.

By composing the coil of the radiopaque material, it is possible to function the reinforcing coil as the radiopaque marker. Thus, it is possible to prevent the flexibility at the front end of the catheter from deteriorating because it is unnecessary to mount the radiopaque marker having a high rigidity on the front end of the catheter.

Further, by making the rigidity of the region of the catheter body at its rear side higher than that of the region thereof at its front side, it is possible to improve the operability of the catheter such as pressing performance, torque transmission performance, follow-up performance, and kink resistance.

The catheter of the present invention can display high kink resistance and pressure resistance without sacrificing the flexibility (low rigidity, bendability) at its front end and has an advantage in making the diameter of its body small. Thus, the catheter is suitably applied to the micro-catheter.

What is claimed is:

1. A catheter having a flexible tubular body and a reinforcing coil embedded in a wall of said body,
wherein said catheter has an outer diameter not larger than 1.5 mm at a front end thereof,
said body has a first region disposed within a range of 1–30 mm from said front end of said catheter and a second region nearer to a rear end of said catheter than said first region;
said coil extends from a position inside said first region to said second region;
a part of said coil disposed in said second region is wound at long winding pitches; and
a winding pitch of a part of said coil disposed in said first region is shorter than that of the part of the coil disposed in said second region and becomes shorter gradually or stepwise toward said front end of said catheter, whereby a rigidity of said catheter is lower in said first region than in said second region.

2. A catheter according to claim 1, wherein said body has a third region nearer to the rear end of said catheter than said second region;
said coil extends from said first region to said third region;
a winding pitch of a part of said coil disposed in said third region is longer than that of the part of the coil disposed in said second region, whereby a rigidity of said catheter is higher in said third region than in said second region.

3. A catheter according to claim 1, wherein a relationship between a winding pitch (S1) of said coil at a rear end of said first region and a winding pitch (E) of said coil at a front end thereof is $E \leq \frac{3}{4} \times S1$.

4. A catheter according to claim 1, wherein a winding pitch of said coil in said first region is in the range of 30 $\mu$m to 300 $\mu$m.

5. A catheter according to claim 1, wherein said coil is made of a radiopaque material.

6. A catheter according to claim 1, wherein a winding pitch of a part of said coil disposed within 5 mm apart from a front end of said catheter is in the range of 30 $\mu$m to 300 $\mu$m.

7. A catheter according to claim 1, wherein a relationship between a winding pitch (S2) of said coil at a position 5 mm apart from a front end of said catheter and a winding pitch (E) of said coil at said front end thereof is $E \leq \frac{3}{4} \times S2$.

8. A catheter according to claim 1, wherein an outer diameter of a part of said catheter disposed within 5 mm apart from a front end of said catheter is less than 1 mm.

9. A catheter according to claim 1, wherein said coil does not have a part in which a winding pitch thereof becomes longer toward a front end of said catheter.

10. A catheter according to claim 1, wherein a part in which said coil is not present is formed at a front end of said catheter.

11. A catheter according to claim 1, wherein the body of said catheter has a rear section and a front section disposed forward from said rear section; and said front section has a lower rigidity than said rear section.

12. A catheter according to claim 11, wherein said front section includes at least an entire length of said first region.

13. A catheter according to claim 1, wherein the body of said catheter has an inner layer and an outer layer; and said coil is embedded between said inner layer and said outer layer.

14. A catheter according to claim 13, wherein said outer layer has a rear section and a front section disposed forward from said rear section; and said front section has a lower rigidity than said rear section.

15. A catheter according to claim 14, wherein said front section of said outer layer includes an entirety of said first region.

16. A catheter according to claim 14, wherein said front section of said outer layer is composed of a polyester elastomer; and said rear section of said outer layer is composed of a polyurethane elastomer having a higher rigidity than said polyester elastomer.

17. A catheter according to claim 1, wherein a part of said inner layer in a thickness direction thereof is in penetration between adjacent windings of said coil.

18. A catheter according to claim 13, wherein said inner layer has a higher rigidity than said outer layer in said first region.

19. A catheter according to claim 13, wherein a hydrophilic polymeric substance is imparted to a surface of at least a front side of said outer layer.

20. A catheter according to claim 1, which accommodates a lumen for a guide wire and can be introduced into a desired portion of a human body along said guide wire which is inserted into said lumen.

21. A catheter according to claim 1, which is used as a micro-catheter.

22. A catheter having a flexible tubular body and a reinforcing coil embedded in a wall of said body,
wherein said catheter has an outer diameter not larger than 1.5 mm at a front end thereof,
a front end of said coil is located within 1–30 mm apart from a front end of said body;
a winding pitch of a part of said coil disposed within 1–30 mm apart from said front end of said body becomes shorter gradually or stepwise toward said front end of said catheter.

23. A catheter according to claim 22, wherein a winding pitch of a part of said coil disposed within 5 mm apart from a front end of said catheter is in the range of 30 $\mu$m to 300 $\mu$m.

24. A catheter according to claim 22, wherein a relationship between a winding pitch (S2) of said coil at a position 5 mm apart from a front end of said catheter and a winding pitch (E) of said coil at said front end thereof is $E \leq \frac{3}{4} \times S2$.

25. A catheter according to claim 22, wherein an outer diameter of a part of said catheter disposed within 5 mm apart from a front end of said catheter is less than 1 mm.

26. A catheter according to claim 22, wherein said coil does not have a part in which a winding pitch thereof becomes longer toward a front end of said catheter.

27. A catheter according to claim 22, wherein a part in which said coil is not present is formed at a front end of said catheter.

28. A catheter according to claim 22, wherein a body of said catheter has a rear section and a front section disposed forward from said rear section; and said front section has a lower rigidity than said rear section.

29. A catheter according to claim 27, wherein said front section includes at least an entire length of said first region.

30. A catheter according to claim 22, wherein the body of said catheter has an inner layer and an outer layer; and said coil is embedded between said inner layer and said outer layer.

31. A catheter according to claim 29, wherein said outer layer has a rear section and a front section disposed forward from said rear section; and said front section has a lower rigidity than said rear section.

32. A catheter according to claim 30, wherein said front section of said outer layer includes an entirety of said first region.

33. A catheter according to claim 30, wherein said front section of said outer layer is composed of a polyester elastomer; and said rear section of said outer layer is composed of a polyurethane elastomer having a higher rigidity than said polyester elastomer.

34. A catheter according to claim 29, wherein said inner layer is made of fluorocarbon resin.

35. A catheter according to claim 29, wherein a part of said inner layer in a thickness direction thereof is in penetration between adjacent windings of said coil.

36. A catheter according to claim 22, wherein a hydrophilic polymeric substance is imparted to a surface of at least a front side of said outer layer.

37. A catheter according to claim 22, which accommodates a lumen for a guide wire and can be introduced into a desired portion of a human body along said guide wire which is inserted into said lumen.

38. A catheter according to claim 22, which is used as a micro-catheter.

39. A catheter according to claim 22, wherein said coil is made of a radiopaque material.

* * * * *

UNITED STATES PATENT AND TRADEMARK OFFICE
CERTIFICATE OF CORRECTION

PATENT NO. : 6,451,005 B1
DATED : September 17, 2002
INVENTOR(S) : Takehiko Saitou et al.

It is certified that error appears in the above-identified patent and that said Letters Patent is hereby corrected as shown below:

<u>Column 24,</u>
Line 58, delete "27" and insert -- 28 --.
Line 64, delete "29" and insert -- 30 --.

<u>Column 25,</u>
Lines 1 and 4, delete "30" and insert -- 31 --.
Lines 9 and 11, delete "29" and insert -- 30 --.

Signed and Sealed this

Twenty-sixth Day of August, 2003

JAMES E. ROGAN
*Director of the United States Patent and Trademark Office*